United States Patent [19]
Giroud-Abel et al.

[11] Patent Number: 5,382,269
[45] Date of Patent: Jan. 17, 1995

[54] ARTIFICIAL SEEDS

[75] Inventors: Bruno Giroud-Abel, Ecully; Francis Molle, Lyons, both of France

[73] Assignee: Rhone-Poulenc Agrochimie, Lyons, France

[21] Appl. No.: 917,131

[22] PCT Filed: Dec. 9, 1991

[86] PCT No.: PCT/FR91/00984

§ 371 Date: Oct. 13, 1992

§ 102(e) Date: Oct. 13, 1992

[87] PCT Pub. No.: WO92/10087

PCT Pub. Date: Jun. 25, 1992

[30] Foreign Application Priority Data

Dec. 10, 1990 [FR] France .................. 90 15740

[51] Int. Cl.⁶ .................. A01C 1/06; A01C 21/00; A01C 1/00; A01B 79/00
[52] U.S. Cl. .................. 47/57.6; 47/58
[58] Field of Search .................. 47/57.601–57.618, 47/57.6, 58

[56] References Cited

U.S. PATENT DOCUMENTS

| | | | |
|---|---|---|---|
| 4,583,320 | 4/1986 | Redenbaugh | 47/57.6 |
| 4,628,633 | 12/1986 | Nilsson | 47/57.6 |
| 4,769,945 | 9/1988 | Motoyama et al. | 47/57.6 |

FOREIGN PATENT DOCUMENTS

| | | |
|---|---|---|
| 117766 | 9/1984 | European Pat. Off. |
| 2046240 | 2/1990 | Japan |
| WO85/02972 | 7/1985 | WIPO |
| WO87/04044 | 7/1987 | WIPO |
| WO91/03149 | 3/1991 | WIPO |
| WO92/07457 | 5/1992 | WIPO |

OTHER PUBLICATIONS

Debergh et al, "Micropropagation", *Kluwer Academic Publisher*, pp. 285–310.

Redenbaugh et al, "Somatic Seeds: Encapsulation of Asexual Plant Embryos", *Biotechnology*, vol. 4, No. 9 (1986) pp. 797–801.

*Primary Examiner*—David T. Fox
*Assistant Examiner*—Erich E. Veitenheimer
*Attorney, Agent, or Firm*—Burns, Doane, Swecker & Mathis

[57] ABSTRACT

Artificial seeds, characterized in that they consist of:
 a meristematic tissue,
 a support in contact with said meristematic tissue, and preferably surrounding said meristematic tissue on all sides, this support being
  a) a solid substance which is not compact and which comprises, in the air and in the dry state, a ratio by volume of air of at least 10%, preferably at least 50%,
  b) permeable to gases and/or vapors, preferably air- and steam-permeable,
  c) dry or dryable,
 a shell made of polymer material and soluble in water, which surrounds the unit composed of support and meristematic tissue,
 a water-tight film which covers the inside of the shell of polymer material.

29 Claims, No Drawings

ARTIFICIAL SEEDS

BACKGROUND OF THE INVENTION

The present invention relates to artificial seeds comprising a meristematic tissue and a solid support.

It is known that artificial seeds have become of increasing interest over recent years, these seeds allowing users to have seeds at hand which comprise homogeneous general features and specific genetic features which are well defined, precise, sophisticated, specific and identified, with a view to obtaining well-determined plant varieties.

It is known that artificial seeds can be made which are embedded in various types of support. In particular, it is well known to produce artificial seeds where a meristematic tissue is embedded in a gel, especially a hydrogel. However, this type of artificial seed has a variety of shortcomings connected to the gels themselves:

- the gels are very susceptible to the action of microorganisms, in particular to the action of fungi or bacteria;
- the gels favorably influence the development of such microorganisms;
- to retain their favorable properties, the gels must generally be preserved under specific humidity and temperature conditions, which makes their long-term storage more complicated.
- in some cases, the gels are formed by pouring liquid in the hot state, which can lead to destruction or, at least, denaturation of the meristematic tissues; it can also have an effect on the preservation of these meristematic tissues, since their keepability can be reduced by the effect of heat.

When gels are formed with the aid of certain substances such as alginates, the ionized molecules which exist in the medium bring about bridge formation between the polymer chains; in consequence, the structure is rendered rigid and the nutrient medium is depleted.

In general, the gels are gas-impermeable, which adversely affects oxygen supply to the meristematic tissues when they need it. To remedy this problem, it has been proposed to implant the meristematic tissue onto the gel, or onto the edge of the gel, so that part of it is in the air, but this is not advantageous since the meristematic tissue is insufficiently protected and, if the artificial seed is turned over and shaken, the tissue can leave the gel, which destroys the unit.

Nutrients and/or protective agents, in particular pesticides, for assisting the development of the artificial seed must be added when the artificial seed is being prepared and not only when growth gets under way, because of the impermeability of the gels. But this addition may not conform to what is really necessary at the point in time when growth of the seed begins.

SUMMARY OF THE INVENTION

It is an aim of the invention to provide an improved artificial seed.

It is another aim of the invention to provide artificial seeds which do not have the shortcomings of the known artificial seeds.

It has now been found that these aims can be achieved fully or partly by means of the seeds according to the invention.

The invention therefore relates to an artificial seed or, in other, words, a capsule comprising:

- a meristematic tissue, that is to say a plant tissue capable of growth so as to give rise to an autonomous and complete plant (or vegetable organism),
- a support in contact with said meristematic tissue, and preferably surrounding said meristematic tissue on all sides, this support being
  a) a solid substance which is not compact and which comprises, in the air and in the dry state, a ratio by volume of air of at least 10 %, preferably at least 50%,
  b) permeable to gases and/or vapors, preferably air- and steam-permeable,
  c) dry or dryable,
- a shell made of polymer material and soluble in water, which surrounds the unit composed of support and meristematic tissue,
- a water-tight film which covers the inside of the shell of polymer material.

The artificial seed can thus be regarded as a system which imparts to meristematic tissue the qualities of being available and handled with ease.

DETAILED DESCRIPTION OF THE PREFERRED EMBODIMENTS

Meristematic tissue is understood as meaning any plant tissue, or group of plant cells, which is capable of developing into a complete plant or part of a complete plant when subjected to suitable conditions. This term embraces any type of plant tissue, especially: somatic tissue, somatic embryos, zygotic tissue, germs, adventitions, buds, shoots, shoot primordia, protocorm-like bodies, green spots, the germ line, and young seedlings.

Naturally, the vegetable organisms to which the invention relates are of a wide range and include food crops such as rice, wheat, barley, maize, soya beans; vegetable crops such as celery, parsley, lettuce, cauliflower, carrot, aubergine, tomato, onion, garlic, ginger, strawberries, melons, asparagus; food crops and/or industrial crops such as oilseed rape, sugar cane, sugar beet, tobacco; medicinal plants such as belladonna, ginseng; ornamental plants such as chrysanthemums, gladioli, lilies, orchids, amaryllis, geraniums, begonias, African violets, poinsettia, trees or tree-like species or shrubs such as conifers, palms, fruit trees, vines, deciduous trees, and others.

Non-compact materials which act as supports for the meristematic tissue and which may be mentioned are fibrous materials (such as wool, cotton or glass wool or rock wool), porous materials, alveolar materials (such as foamed synthetic polymers, in particular polyethers and polyurethanes). More particularly, there may be mentioned sand, clay, vermiculite, glass beads, cotton, paper, cereal bran, sawdust, wool and others.

The water-tight film is essentially composed of a film-forming substance which has by nature hydrophobic properties and/or the property of being impermeable to liquid water.

The following may be mentioned from amongst these substances: synthetic polymers, natural polymers, artificial polymers and film-forming substances which are not polymers.

Examples which may be mentioned of synthetic polymers which can be used according to the invention are vinyl resins, in particular polyethylene, polypropylene, polystyrene, polymethyl methacrylate, polyvinyl chloride, polyvinylidene fluoride, polyvinyl fluoride, polyvinylidene chloride, polychlorotrifluoroethylene, polyethylene terephthalate, polyvinyl acetate, ethylene/vinyl ester copolymers; formaldehyde- or butyraldehyde-based vinyl polymers; polyesters, especially polyethylene terephthalate; polycarbonates; polyamides, especially poly(11-aminoundecanamide) or nylon 11; polyethers, especially polyphenylene oxide; polychloroprene, polyisoprene, polyurethanes, butyl rubber, and silicones, especially organopolysiloxane polymers.

Examples of natural polymers which may be mentioned are gutta percha and natural rubber.

Examples of artificial polymers which may be mentioned are the water-impermeable cellulose derivatives, especially ethylcellulose, cellulose acetate, cellulose propionate, and nitrocellulose.

Examples which may be mentioned of film-forming substances which are not polymers are the fats and waxes, especially palm oil and copra oil.

The water-tight film inside the water-soluble polymer shell can be made using a variety of methods known per se, preferably by coating, for example by spray-coating or by painting.

In this coating process, solutions or emulsions or suspensions may be used.

The water-tight film generally has a thickness of between 1 and 250 microns, preferably between 5 and 100 microns.

Examples which may be mentioned of water-soluble polymers which can constitute the shell are gelatin, casein, starch, alginates, methylcellulose, hydroxyethylcellulose and, more generally, the (lower) hydroxyalkylcelluloses, polyvinyl alcohol, the polyacrylates (acid or salts), polyacrylamide, polyethylene oxide, and polyvinyl-pyrrolidone.

The shell of water-soluble polymer is preferably rigid in the dry state, but this rigidity does not exclude a certain pliability and a certain flexibility.

In general, the thickness of the shell made of water-soluble polymer is between 0.1 and 5 mm, preferably between 0.25 and 1.5 mm.

Besides the various components which have already been described, the artificial seeds can further contain a variety of other types of additives or adjuvants, especially fertilizers, fungicides, bactericides, trace elements, and nutrients.

These various compounds can exist mixed with the support and/or incorporated into the shell wall of water-soluble polymer.

When the artificial seeds contain the quantity of water (provided, for example, by an aqueous nutrient solution mixed with the support) necessary for the development of the meristematic tissue they may be stored in the cold, for example between 0° and 10° C., preferably in a dry atmosphere such as that having a relative humidity less than 50%, in order to avoid premature development of the meristematic tissue. This development will be accomplished once the artificial seeds return to ambient temperature (20–25° C.).

At the time of their use, the seeds are placed in known manner on a moist culture substrate such as, for example, sand, compost, peat or vermiculite. On contact with the water contained in the said substrate, the soluble polymer shell swells and then either dissolves or softens forming a gel which no longer has mechanical resistance. During this time the water-tight film (covering the inside of the shell) disintegrates under the pressure of the plant organs produced by growth of the meristematic tissue, for example the roots, and these plant organs can penetrate without difficulty into the culture substrate when the polymer shell has lost its mechanical resistance as indicated above.

When the artificial seeds do not contain the quantity of water necessary for development of the meristamatic tissue they may be stored at ambient temperature. In this case, provision of the water necessary for development of the said tissue may be provided at the time the seeds are used, for example, by providing the seeds in the form of capsules equip with a removable cover, by removing the said cover and then watering the interior of the capsules.

The examples which follow are given not by way of limitation and are intended to illustrate the invention and its application in practice without restricting it to a particular method.

EXAMPLE 1

A gelatin capsule (polymer shell) is used which is composed of a receptacle portion and a lid portion; this capsule has an outer dieter of 4 mm, a length of 1 cm for the receptacle portion and 1 cm for the lid portion (the receptacle and lid are fitted together with an overlap of 5 mm). The wall has a thickness of 0.5 mm. The wall is composed of gelatin (water-soluble natural polymer) which barn been plasticized with the aid of glycerol.

The inside of this capsule is covered with an 0.1 mm layer of polyvinyl chloride. The coating process is carried out by pouring onto the inside of the capsule a polymer solution in a concentration of 2.5% in tetrahydrofuran, and then eliminating this same solution by turning the capsule over and allowing the solution to run out, followed finally by drying in the air.

Into the capsule which has been prepared in this manner, the following items are introduced in succession under sterile conditions:

sterile hydrophilic cotton wool (100 mg), followed by
an aqueous nutrient solution (1 cc) containing sucrose (15 g/l) and mineral salts (composition as described by Murashige and Skoog, Physiol. Plant. vol. 15, pages 473–497, 1962.),
a somatic carrot embryo (*Daucus carota*) which is deposited on the cotton wool soaked with nutrient solution.

Ten capsules are prepared in the same fashion, but using different types of support within which the capsules are placed; vermiculite and glass beads are used in this way. After the capsules have been prepared, they are sealed by fitting the lid.

The capsules are then stored for one month at 4° C. in a dry atmosphere, that is to say at a relative humidity of 40%. The same capsules are then placed within a moist support composed of sand (average particle size 0.5 mm), and the unit is placed into a closed incubator at 24° C. at a relative humidity of 80 % and a day/night rhythm of 14/10 hours.

The external wall of the capsules swells and softens.

After 7 days, the emergence of chlorophyll-containing cotyledons is observed which, at the time, come through the softened capsule wall. After 15 days, the appearance of the first true leaves can be observed.

EXAMPLE 2

Example 1 is repeated, but with the following variations: the inside of the capsule is coated with the aid of a solution containing 15 % of polyvinyl acetate and 10% of polylactide in acetone.

Vermiculite (80 mg) is introduced into the capsule, and then the nutrient solution used in Example 1 (2 cc).

The somatic embryos develop in the same fashion as in Example 1.

We claim:

1. An artificial seed which comprises:
   a) an isolated meristematic tissue derived from somatic or zygotic embryos,
   b) a support in contact with said isolated meristematic tissue, said support surrounding said isolated meristematic tissue on all sides, wherein the support is:
      i) a solid substance which is not compact and which comprises, in the air and in the dry state, a ratio by volume of air of at least 10%,
      ii) permeable to gases and/or vapors,
      iii) dry or dryable, and
      iv) fibrous, porous or alveolar;
   c) a shell made of polymer material and soluble in water, which surrounds the unit composed of support and meristematic tissue, and
   d) a water-tight film which covers the inside of the shell of polymer material.

2. The seed of claim 1, wherein the isolated meristematic tissue is derived from a plant which is a food crop.

3. The seed of claim 1, wherein the water-tight film is essentially composed of a film-forming substance which has by nature hydrophobic properties and/or the property of being impermeable to liquid water.

4. The seed of claim 3, wherein the water-tight film is based on synthetic polymers, natural polymers, artificial polymers or film-forming substances which are not polymers.

5. The seed of claim 4, wherein the water-tight film is based on a polymer.

6. The seed of claim 1, wherein the water-tight film has a thickness of between 1 and 250 microns, 7. The seed of claim 1, wherein the sheet is composed of gelatin, casein, starch, alginates, methylcellulose, hydroxyethylcellulose (lower) hydroxyalkylcelluloses, polyvinyl alcohol, polyacrylates (acid or salts), polyacrylamide, polyethylene oxide, or polyvinylpyrrolidone.

8. The seed of claim 1 wherein the shell of water-soluble polymer has a thickness of between 0.1 and 5 mm.

9. The seed of claim 1, wherein the support for the isolated meristematic tissue is wool, cotton, glass wool, rock wool, a foamed synthetic polymer, sand, clay, vermiculite, glass beads, paper, cereal bran or sawdust.

10. The seed of claim 2, wherein the food crop is rice, wheat, barley, maize or soya bean.

11. The seed of claim 1, wherein the isolated meristematic tissue is derived from a plant which is a vegetable crop.

12. The seed of claim 11, wherein the vegetable crop is celery, parsley, lettuce, cauliflower, carrot, aubergine, tomato, onion, garlic, ginger, strawberry, melon or asparagus.

13. The seed of claim 1, wherein the isolated meristematic tissue is derived from a plant which is an industrial crop.

14. The seed of claim 13, wherein the industrial crop is oilseed rape, sugar cane, sugar beet or tobacco.

15. The seed of claim 1, wherein the isolated meristematic tissue is derived from a plant which is a medicinal plant.

16. The seed of claim 15, wherein the medicinal plant is belladonna or ginseng.

17. The seed of claim 1, wherein the isolated meristematic tissue is derived from a plant which is an ornamental plant.

18. The seed of claim 17, wherein the ornamental plant is a chrysanthemum, gladiolus, lily, orchid, amaryllis, geranium, begonia, African violet, or poinsettia.

19. The seed of claim 1, wherein the isolated meristematic tissue is derived from a tree, tree-like species or shrub.

20. The seed of claim 19, wherein the tree is a conifer, palm, fruit tree or deciduous tree.

21. The seed of claim 5, wherein the polymer is polyethylene, polypropylene, polystyrene, polymethyl methacrylate, polyvinyl chloride, polyvinylidene fluoride, polyvinyl fluoride, polyvinylidene chloride, polychlorotrifluoroethylene, polyethylene terephthalate, polyvinyl acetate, an ethylene/vinyl ester copolymer, polycloroprene, polyisoprene, polyurethane, polyester, polycarbonate, polyamide, polyether, butyl rubber, silicone-based polymer, or formaldehyde- or butyraldehyde-based vinyl polymer.

22. The seed of claim 21, wherein the polyester is polyethylene terephthalate.

23. The seed of claim 21, wherein the polyamide is poly(11-aminoundecanamide).

24. The seed of claim 21, wherein the polyether is polyphenylene oxide.

25. The seed of claim 21, wherein the silicone-based polymer is an organopolysiloxane polymer.

26. The seed of claim 1, wherein said ratio by volume of air is at least 50%.

27. The seed of claim 1, wherein the support is air- and steam permeable.

28. The seed of claim 6, wherein the water-tight film has a thickness of between 5 and 100 microns.

29. The seed of claim 8, wherein the shell of water-soluble polymer has a thickness of between 0.25 and 1.5 mm.

* * * * *